(12) United States Patent
Norton

(10) Patent No.: US 7,145,654 B2
(45) Date of Patent: Dec. 5, 2006

(54) METHOD AND APPARATUS TO REDUCE SPOTSIZE IN AN OPTICAL METROLOGY INSTRUMENT

(75) Inventor: Adam E. Norton, Palo Alto, CA (US)

(73) Assignee: Tokyo Electron Limited, Tokyo (JP)

( * ) Notice: Subject to any disclaimer, the term of this patent is extended or adjusted under 35 U.S.C. 154(b) by 293 days.

(21) Appl. No.: 10/957,249

(22) Filed: Oct. 1, 2004

(65) Prior Publication Data

US 2005/0073684 A1    Apr. 7, 2005

Related U.S. Application Data

(60) Provisional application No. 60/507,731, filed on Oct. 1, 2003.

(51) Int. Cl.
*G01J 4/00* (2006.01)

(52) U.S. Cl. ................................. 356/369

(58) Field of Classification Search ............ None
See application file for complete search history.

(56) References Cited

U.S. PATENT DOCUMENTS

| | | | |
|---|---|---|---|
| 4,710,642 A | 12/1987 | McNeil | 250/559.04 |
| 5,164,790 A | 11/1992 | McNeil et al. | 356/496 |
| 5,329,357 A | 7/1994 | Bernoux et al. | 356/369 |
| 5,379,150 A * | 1/1995 | Miyazaki et al. | 359/561 |
| 5,442,172 A * | 8/1995 | Chiang et al. | 250/237 G |
| 5,607,800 A | 3/1997 | Ziger | 430/8 |
| 5,739,909 A | 4/1998 | Blayo et al. | 356/369 |
| 5,798,837 A | 8/1998 | Aspnes et al. | 356/369 |
| 5,859,424 A | 1/1999 | Norton et al. | 250/226 |
| 5,867,276 A | 2/1999 | McNeil et al. | 356/445 |
| 5,910,842 A | 6/1999 | Piwonka-Corle et al. | 356/369 |
| 5,963,329 A | 10/1999 | Conrad et al. | 356/613 |
| 6,483,580 B1 | 11/2002 | Xu et al. | 356/300 |
| 6,590,660 B1 * | 7/2003 | Jung et al. | 356/419 |

* cited by examiner

*Primary Examiner*—Tu T. Nguyen
(74) *Attorney, Agent, or Firm*—Stallman & Pollock LLP

(57) ABSTRACT

The measurement spot size of small-spot reflectometers, ellipsometers, and similar instruments can be reduced by placing an optical fiber along the optical path of the instrument, such as between an illumination source and a sample or the sample and a detector. The angular range of the probe beam can be adjusted to be less than a natural numerical aperture of the optical fiber. A multimode fiber can be used, which can have a controllable amount of bend or coil, such that rays entering the fiber at larger angles of incidence are attenuated more than rays entering at shallow angles of incidence. Light passing through the fiber can be selectively attenuated and partially mixed to reduce the presence of secondary maxima falling outside the measurement spot. Minimizing these secondary maxima can improve the amount of light measured by the detector that is reflected from inside the measurement spot.

46 Claims, 2 Drawing Sheets

METHOD AND APPARATUS TO REDUCE SPOTSIZE IN AN OPTICAL METROLOGY INSTRUMENT

CLAIM OF PRIORITY

This application claims priority to U.S. Provisional Patent No. 60/507,731, entitled "METHOD AND APPARATUS TO REDUCE SPOTSIZE IN AN OPTICAL METROLOGY INSTRUMENT," filed Oct. 1, 2003, which is hereby incorporated herein by reference.

TECHNICAL FIELD OF THE INVENTION

The subject invention relates to optical devices and techniques for the non-destructive evaluation of samples such as semiconductor wafers.

BACKGROUND

There is a great need in industries such as the semiconductor industry for sensitive metrology equipment that can provide high resolution and non-contact evaluation capabilities, particularly as the geometries of devices in these industries continue to shrink. Manufacturers have increasingly turned to optical metrology techniques, such as ellipsometry and reflectometry, which typically operate by illuminating a sample with a probe beam of electromagnetic radiation and then detecting and analyzing the reflected and/or transmitted energy. The probe beam can consist of polarized or unpolarized radiation, and can include one or more wavelengths of radiation in any of the appropriate radiation bands as known in the art. Ellipsometry techniques typically measure changes in the polarization state of the reflected beam after interacting with the sample, while reflectometry techniques measure changes in the magnitude of the reflected beam. Scatterometry is a specific type of optical metrology that typically is used to measure diffraction, or optical scattering, of the probe beam due to the structural geometry of the sample, whereby details of the structure causing the diffraction can be determined.

These metrology techniques can be used to analyze a wide range of parameters, such as the thickness, crystallinity, composition, and refractive index of a film on a silicon wafer, for example. Measurements of this type can be made using reflectometry or ellipsometry techniques as described more fully in U.S. Pat. Nos. 5,910,842 and 5,798,837, each of which is hereby incorporated herein by reference. Other attributes of a sample that can be measured include critical dimensions (CD), line spacing, line width, wall depth, and wall profiles. Measurements of this type can be obtained using monochromatic scatterometry, such as is described in U.S. Pat. Nos. 4,710,642 and 5,164,790, each of which is hereby incorporated herein by reference. Another technique involves the use of broadband light to perform multiple wavelength spectroscopic reflectometry measurements. Examples of this approach can be found in U.S. Pat. Nos. 5,607,800; 5,867,276; and 5,963,329, each of which is hereby incorporated herein by reference. Other techniques utilize spectroscopic ellipsometric measurements, such as can be found in U.S. Pat. Nos. 5,739,909 and 6,483,580, each of which is hereby incorporated herein by reference.

When using one of these optical metrology techniques, it can be desirable to measure only a small region of a sample in a measurement box when there are a number of features and/or areas of different materials and/or concentration near the measurement box. A measurement box generally refers to a portion of the surface of a sample that is to be measured, and often is determined by structures and/or features of the sample. Using a large measurement spot could allow the measured signal to include multiple of these features and/or areas, which can be difficult to discern during signal analysis. For example, in order to measure the thickness of a film on a semiconductor wafer it can be necessary to utilize a measurement spot on the order of about 10 microns in order to avoid measuring features of nearby integrated circuits. Confining measurements to a small region is especially difficult for optical metrology devices that utilize probe beams at non-normal angles of incidence. In ellipsometers that can have incidence angles on the order of about 75°, for example, the high angle of incidence beams, of some diameter, project to a spot on the sample that has dimensions larger than the beam diameter. Also, at non-normal incidence, the deleterious effects of diffraction to enlarge the measurement spot, discussed below, can become more pronounced. Even for metrology systems that utilize near-normal angles of incidence the diffraction due to hard stops can cause difficulty in obtaining such small spot sizes.

FIG. 1 shows an exemplary optical metrology arrangement 100 of the prior art that can be used to capture ellipsometry and/or reflectometry data. The arrangement includes an illumination source 102 that creates a monochromatic or polychromatic probe beam 104. Any pinholes, apertures, or even optics of a finite size can comprise stops, which typically are used to control various aspects of the system. The probe beam. 104 is focused by one or more lenses 106 and/or other optical focusing elements to create an illumination spot on the surface of the sample 108 being examined. The illumination optics typically include an illumination pinhole 110 to help control the illuminated spot on the sample, and an illumination aperture 118 to help control the angular spectrum of the illumination. The angular spectrum refers to the distribution of light propagating at different angles with respect to a central ray of the system. The illumination aperture is typically at a focal plane of the illumination lens 106. The arrangement also can include at least one additional lens 112 and/or other optical focusing elements for collecting light reflected from the sample, in order to project the light onto the detector 114. A detection pinhole 116 and a detection aperture 120 can be used to select a portion of the light reflected from the illumination spot, which is to be projected onto the detector 114. If a laser is used as the illumination source, one or more of the pinholes and apertures on the collection and/or illumination sides may not be needed.

A goal of such a system is to allow the measurement spot to fall completely within the measurement box. The measurement spot refers to that portion of the surface from which light is reflected and subsequently received by the detector. The measurement spot can be controlled by aspects of the illumination and detection optics. The measurement box, in turn, typically is determined by structures or features of the sample, as the measurement box often is that portion of the surface of the sample that has a feature to be measured. In some cases, physical squares or boxes are manufactured onto the surface of a sample, such as a semiconductor wafer, in order to facilitate such measurements. In other cases, these boxes are merely conceptual regions. In general, there can be different measurement sensitivities at various locations within the measurement spot. A typical measurement spot does not have sharp edges or boundaries, but has a spatial distribution of measurement sensitivity. The spatial distribution of measurement sensitivity within the measurement spot can be affected by, for example, the illumination pinhole, the illumination aperture, the detection aperture, the detection pinhole, and aberrations in the optics. It can be desirable to have the measurement sensitivity as spatially confined as possible.

Chromatic aberration can limit the desired confinement of the measurement spot, and further can preclude use of a refractive optical element when using a broadband source. Reflective optics can be used to reduce chromatic aberration, but reflective optics may not be appropriate as the optics can partially polarize the beam and prevent, for example, accurate ellipsometry measurements. A significant problem that exists when using hard stops for pinholes and apertures is that the measurement spot will not have perfectly sharp edges, due to diffraction of the light. The measurement sensitivity will typically have a main lobe surrounded by secondary maxima, or broad areas of low-level sensitivity, sometimes referred to in the industry as "tails." Such tails can arise from the illumination optics or from the detection optics.

A goal when designing a small spot instrument using an arrangement such as that shown in FIG. 1 is to minimize the ratio of light collected by the detector that is reflected from the area outside the measurement box versus the light reflected from inside the measurement box on the sample. One way to minimize this ratio in practice is to minimize the tails of the measurement sensitivity. The tails can be minimized in one approach by making the illumination and collection spots approximately the same size. Such a system is sometimes referred to as a confocal system. This is not always practical, however, as the instrument becomes extremely sensitive to focus and/or alignment errors. Such alignment can be difficult to maintain where the system experiences temperature, pressure, or other variations, or where the system requires shipping and/or movement. It therefore can be more practical to allow one of the illumination and collection spots to be larger than the other. While the smaller of the two spots can have the greatest influence on the measurement spot size, diffraction from both the illumination and collection optics still can have a significant effect on the tails of the measurement spot.

One technique that is used in the art to control the presence of tails is known as apodization. The McGraw-Hill Dictionary of Scientific and Technical Terms, 2nd Ed., 1985, by McGraw-Hill, Inc., defines "apodization" as "The modification of the amplitude transmittance of the aperture of an optical system so as to reduce or suppress the energy in the diffraction rings relative to that of the central Airy disk." Apodization can be used to change the transmission characteristics of an aperture to attenuate the rings or tails. This can be done, for example, by replacing a traditional hard stop or the aperture with a tapered stop that has a gradual transition between transmissive and opaque regions. Diffraction typically arises from edges and sharp transitions, and a tapered stop will have a less well-defined edge. An optical system including such a tapered stop can produce a measurement spot with smaller tails. Apodization in optical metrology systems is discussed in U.S. Pat. No. 5,859,424, which is hereby incorporated herein by reference. For apodization, light is attenuated as a function of position on an apodizing filter containing a two-dimensional half-tone pattern, a pattern of alternating high transmittance areas and substantially opaque areas. While such an apodizing filter can be effective, the filter cannot be placed close to conjugates of the sample where the half-tone pattern of the filter would interfere with patterns on the sample. The filter is preferably placed near a focal plane of the optics or one of its conjugates, so the half-tone pattern does not project onto the sample. This placement constraint can be a disadvantage for various implementations and/or applications. Another problem with such apodizing filters is that in systems where a polarizer is close to the source, such as is described in U.S. Pat. No. 5,859,424, the apodizing filter must be placed at a position where the light is polarized. This can be problematic, as birefringence of the apodizing filter can disturb the polarization state. Another problem is that the apodizing filter works by blocking some of the light with which the filter is illuminated. To work properly, the entire half-tone pattern should be illuminated. The half-tone pattern therefore blocks some of the light with which it is illuminated in order to achieve the desired effect. Further still, a two-dimensional apodizing filter can be difficult to design and produce with regularity, can require precise alignment, and can be relatively expensive.

DETAILED DESCRIPTION

Systems and methods in accordance with various embodiments of the present invention can overcome these and other deficiencies in existing small-spot optical measurement devices by changing the way in which the measurement spot size is controlled. Such control allows for a reduction in the diffraction tails produced by hard stops, reducing the measurement spot size within these metrology systems. Systems and methods in accordance with embodiments of the present invention avoid the need for apodization, instead introducing a variation in the angular spectrum of the illumination and/or detection sensitivity using an optical fiber. Such an approach avoids problems associated with apodization such as those discussed above.

Figure 2A:
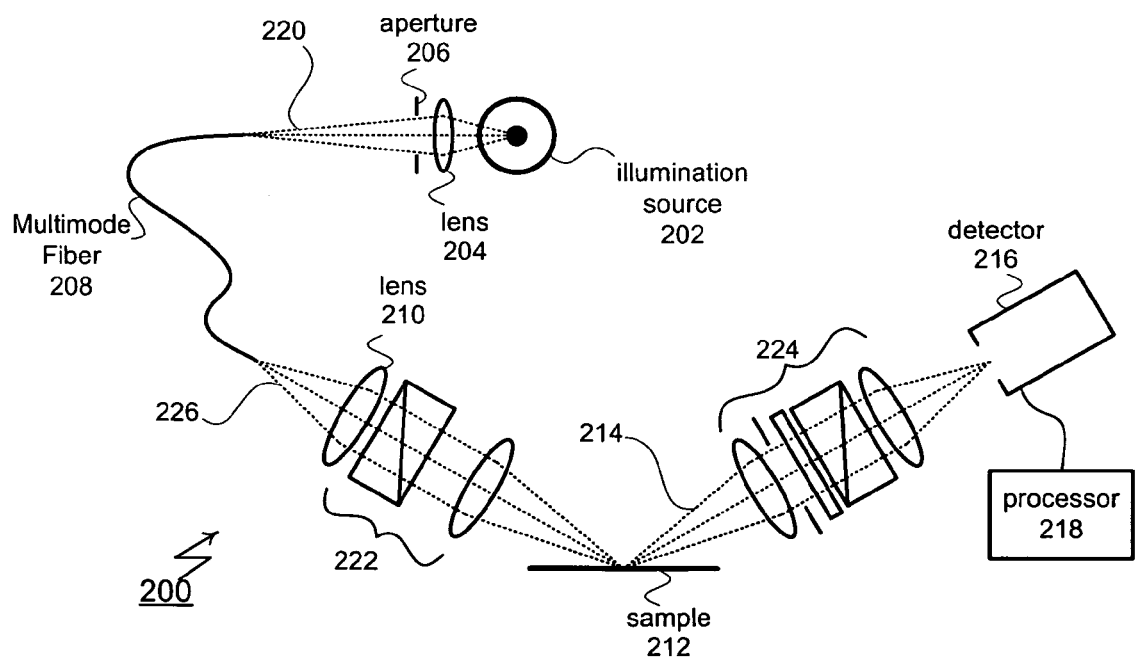
FIG. 2(a) is a block diagram of an ellipsometer configured to include an optical fiber on the illumination side in accordance with one embodiment of the present invention.

FIG. 2(a) shows an optical arrangement 200 in accordance with one embodiment of the present invention. While the arrangement will be described with respect to an ellipsometer system, such a technique for reducing the measurement spot size can be used for any of a number of small-spot reflectometers, ellipsometers, and similar optical metrology instruments. In FIG. 2(a), an ellipsometer is shown that includes an illumination source 202 that produces fiber illumination 220. The illumination source can be any appropriate illumination source, such as a laser, Xenon arc lamp, a deuterium lamp, an LED, or a tungsten bulb. The illumination can be collected by a lens 204 to be focused on an entrance end of an optical fiber 208. Depending upon the width of the fiber illumination, the width of the fiber, and the focusing element used, a hard stop 206 can be used to limit the numerical aperture of the fiber illumination incident upon the end of the fiber 208. Focusing element 204 can be used to collect and control the fiber illumination, such as to control the angular spread of light entering the fiber. In order to control the spot size and/or presence of tails about the spot produced by the light on the sample, as discussed below, the fiber can be illuminated with a numerical aperture that is limited by lens 204 and/or hard stop 206 to be smaller than the numerical aperture (NA), of the fiber. The NA of a fiber is a measure of the ability of an optical fiber to capture and transmit light at various angles, and is used in industry to define the acceptance cone of the fiber. Typical values of NA range from 0.20 to 0.29 for glass fibers. Plastic fibers generally have larger NAs, such as on the order of 0.50 or higher.

The fiber illumination 220 is transported by fiber 208 to produce probe beam 226. The probe beam 226 exiting the fiber can be collected by a lens 210, then conditioned and focused onto the sample by illumination conditioning optics 222. The illumination optics can include any appropriate optical elements, such as for example a polarizer element. At least a portion of the probe beam 226 can be reflected from the sample as sample reflection 214 and collected by a lens and/or other collection optics and/or conditioning optics 224. The collected sample reflection can be conditioned by the reflection conditioning optics 224 before being incident upon a detector 216. The detector can include any appropriate detection and/or measurement device known or used in the art for such an optical metrology system, such as a monochromer or spectrometer. The detector 216 can measure the intensity of the sample reflection after the reflection has passed through reflection conditioning optics 224, and can generate a measurement output signal in response thereto. For example, the reflection conditioning optics 224 may contain a rotating compensator and analyzer. The output signal can be received by a processor 218 or computer device that can analyze the output signal to determine structural and/or material details of the sample 212. For example, the computer may control the rotation of a rotating compensator in reflection conditioning optics 224, receive output signals at different known rotations, and extract ellipsometric parameters from the data possibly to be used for further processing.

The measurement spot size can be controlled, at least in part, by the optical fiber 208 used to transport the illumination. The fiber 208 can be any appropriate optical fiber, such as a multimode fiber optic having an exit face conjugate to (i.e. imaged onto) the sample 212. The multimode fiber can be a graded index fiber, with a bandwidth of about 800 MHz*km and a core diameter in the range of 50–100 µm, or a step index fiber, with a bandwidth of about 20 MHz*km and a core diameter in the range of 100–250 µm, for example. The fiber can be a standard optical fiber, for example, having a glass core, glass cladding, and a thermoplastic overcoating; a plastic optical fiber (POF); or a fiber with a silica core and doped silica cladding (of a lower refractive index), having a coating of transparent plastic (e.g., acrylate), polyimide, or metal. The spread of angles that can be propagated down the fiber can be dependent upon the selected fiber, as known in the art.

The optical fiber 208 produces a probe beam 226 having an angular spectrum, whereby the intensity of the probe beam varies as a function of propagation angle relative to the optical axis. The shape of the angular spectrum is the result of fiber illumination, propagation attenuation and mode mixing within the fiber. The exit end of the fiber 208 can be effectively placed at or near a conjugate of the sample, as in the case shown, where the end of the fiber is focused on the sample. Appropriate optical fibers for such an application are readily available, can be purchased in bulk, and can be obtained from a number of sources. The effect of the fiber on the polarization state of the probe beam is irrelevant to the operation of the instrument as shown in this embodiment, because the first polarization sensitive component appears later in the optical chain, here in the illumination conditioning optics 222. The fiber is a waveguide used to transport the source illumination to the rest of the optical system. Other appropriate waveguides, such as a hollow waveguide, can be used to transport the illumination that would not suffer from propagation loss. Illumination propagates down the length of the fiber as rays excited by the angular spectrum of the fiber illumination 220. As those rays propagate along the length of the fiber, the rays can mix and/or become somewhat scrambled. In addition, rays propagating with higher angles, corresponding to higher initial angles of incidence at the entrance end, are more strongly absorbed in the fiber cladding than rays propagating at lower angles. Thus the edges of the angular spectrum of the probe beam will be less intense than a central region of the angular spectrum of the probe beam. The extent to which the propagation angles mix and/or are absorbed in the cladding can be a result of a number of factors, including the construction of the fiber, length of the fiber, amount of bending and/or coiling of the fiber along the transportation path, and the light input NA.

Figure 1:
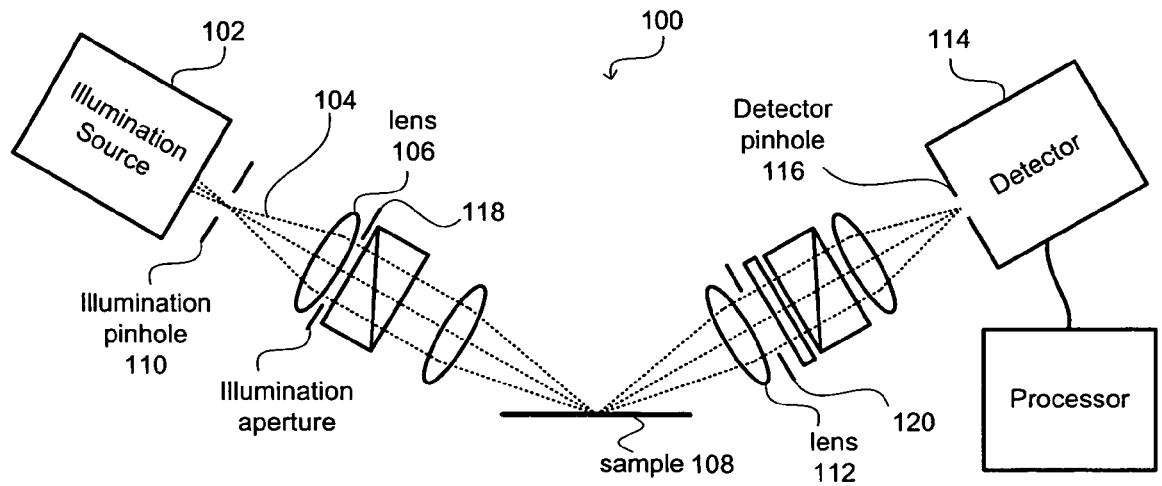
FIG. 1 is a block diagram of an ellipsometer or reflectometer system of the prior art.

Various mechanisms are available to allow the angular spectrum to gradually taper from a larger value nearer the center to a lower value at the edge. For example, the NA of focused fiber illumination incident upon the entrance end of the fiber can be smaller than the NA of the fiber, as discussed above. Mixing will cause the angles that have not been illuminated to contribute, to some extent, to the exiting probe beam. This effect offers additional control of the angular spectrum of the probe beam. The angular spectrum propagating down the fiber then can be controlled to some extent by adjusting the shape or configuration of the fiber, such as by bending and/or coiling the fiber by a specific amount. This bending can be done manually or automatically, either during testing and setup or as part of a feedback loop during operation. The bending of a fiber can exaggerate the angles at which rays are propagating down the fiber relative to a central axis of the fiber. These exaggerated angles can cause the rays to be more likely to be absorbed into the cladding, such that the portion of rays traveling at smaller angles relative to the central axis is increased with respect to the portion of rays traveling at larger angles. This attenuation of rays propagating at higher angles can affect the angular spectrum of the beam exiting the fiber, having significantly more energy propagating at small angles relative to the optical axis than at larger angles. After the probe beam 226 exits the fiber, a focusing element can collect and focus the beam onto the sample. When the probe beam reaches the focusing optic(s) 210, a central portion of the beam will be significantly brighter than the region near to the edge of any stop(s) in the optics, such as on the order of about 30% brighter. By adjusting and/or carefully selecting the fiber parameters, the distribution of light at the plane of any stop associated with the imaging optics 222 can substantially decrease gradually towards the edge of the stop. This is in contrast to the situation if FIG. 1, where the illumination aperture is a hard stop that is typically fully illuminated and controls the angular distribution of light at the sample. The hard aperture induces diffraction, which leads to tails in the illumination sensitivity at the sample and a subsequent enlargement of the measurement spot. Any of the illumination or collecting optics can act as an aperture for the probe beam or sample reflection. Any of these elements can be prevented from acting as a diffracting hard stop if the intensity of the light hitting the edge of the stop is substantially reduced relative to light going through the stop further from its edge. This can be achieved by controlling the sizes of the optics and the angular spectrum of the illumination.

In the prior art of apodization, the amplitude transmittance of the aperture is modified to avoid the deleterious of effects of diffraction. In the present invention, the transmittance in the aperture need not be modified, as the shape and size of the probe beam can be controlled so that any diffraction-inducing edges are not significantly illuminated. The effect of the fiber on the illumination allows a relatively smaller illumination spot to be created on the sample because the intensity tapers away from the optical axis before hitting any hard stop, thus avoiding diffraction effects. Correct use of an illumination fiber thus can reduce the tails of the beam by reducing diffraction, thereby permitting measurement in a smaller measurement box.

Figure 2B:
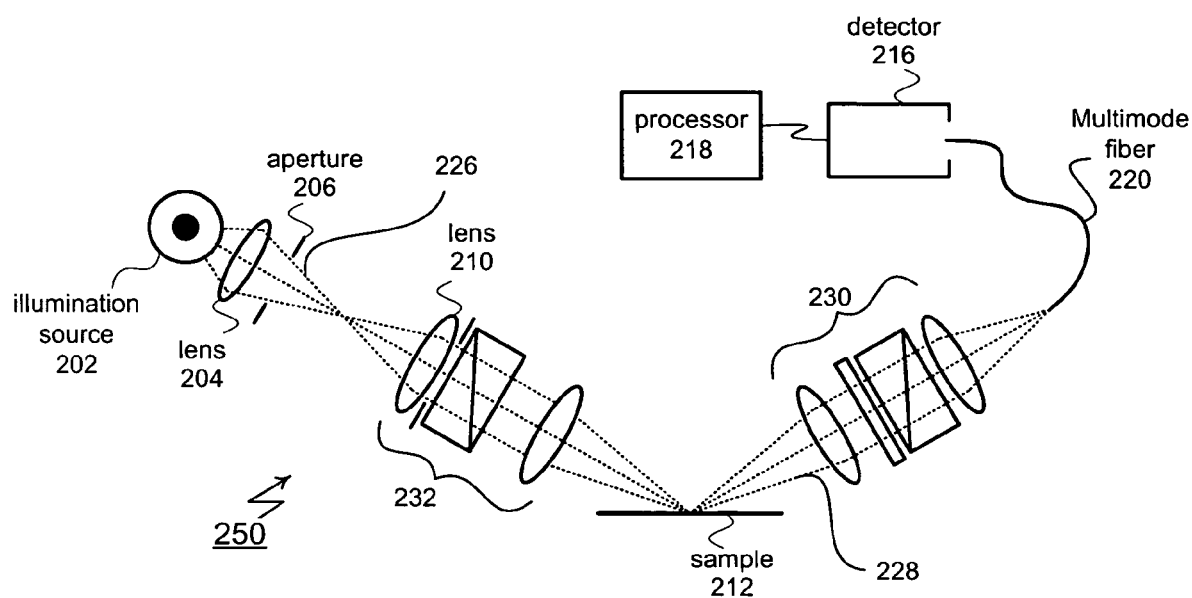
FIG. 2(b) is a block diagram of an ellipsometer configured to include an optical fiber on the collection side in accordance with one embodiment of the present invention.

FIG. 2(b) shows a second optical arrangement 250 in accordance with one embodiment of the present invention. Reference numbers are carried over where appropriate for the sake of simplicity, and this arrangement will again be described with respect to an ellipsometer but could be applicable to any of a number of optical metrology devices. Light from an illumination source 202 is collected by a lens 210, then conditioned and focused onto the sample by illumination conditioning optics 232. In this arrangement, a detection fiber 220 is placed on the detection side of the sample 212, between the sample 212 and the detector 216. The effect of the fiber on measurement spot size is reciprocal to the effect of the illumination fiber 208 in FIG. 2(a). In FIG. 2(a) the intensity of light propagating through the illumination system was the primary concern. Here, the detection sensitivity is of a primary concern. The input face of the detection fiber 220 acts as a detection pinhole. Detection focusing optics 230 can collect the reflected light 228 and focus the reflected light onto the entrance of the detection fiber 220. The detection fiber can have a numerical aperture as described above, and the detector can have a numerical aperture specifying the angular spectrum over which the detector detects incoming light. The numerical aperture of the detector 216 can be less than that of the detection fiber 220, thus giving control of the reflection sensitivity reciprocal to the control of the illumination achieved in FIG. 2(a) by illuminating the end of fiber 208 with a cone of illumination 220 that is narrower than the NA of fiber 208.

The light reflected from the surface of the sample that is collected and focused on the end of the fiber will have an angular spectrum relative to a central axis of the fiber. As discussed above, the angular spectrum gives rise to various rays which can mix and/or become somewhat scrambled as those rays propagate through the fiber. Rays with higher incoming angles can be more strongly absorbed in the fiber cladding, thus having reduced detection sensitivity. Specifically, rays due to diffraction from the any hard stop in the detection optics 224 can have high incoming angles at the fiber 220 and be detected with reduced sensitivity. Thus the effects of diffraction from any stop, such as the edge of the clear aperture of optics 224, would be substantially reduced. Again, the length and amount of bending of the fiber along the transportation path can be used to adjust the angular spectrum detection sensitivity. Also, when numerical aperture of the detector 216 is less than that of the detection fiber 220, the detection sensitivity to the angular spectrum of reflected light 228 decreases more gradually towards the edge of that spectrum. By reducing diffraction effects with a gradual reduction, the measurement sensitivity will not exhibit strong secondary maxima or tails, and can fit more easily within smaller measurement boxes.

In any spectroscopic ellipsometer arrangement, broadband light from a source such as a Xenon arc lamp can be passed through a polarizer that is rotated as known in the art. The polarizer can produce an undeviated beam that is linearly polarized with a first polarization vector, and a deviated beam that is polarized perpendicular to the undeviated beam. The undeviated beam can be focused onto the sample using any appropriate optical element, such as a focusing mirror. The ability of this focusing element to focus the probe beam on the sample, as well as the angles of reflection that can be captured by the collection optics, can determine the area on the sample that can be measured. The collection optics can focus the reflected light on a detector element, such as an entrance slit of a spectrometer. Before reaching the detector, the light can pass through any folding or directing optics, as well as an analyzer, which can be computer controlled to select light of a single polarization. The area of the sample that is focused by the collection optics can be larger than the illuminated area, or vice versa, in order to facilitate alignment of the system optics. The detector can measure a single wavelength or various wavelength components of the reflected probe beam, and can provide an output signal including information about the phase and/or amplitude of the reflected probe beam. A processor can use this output signal to determine characteristics of the sample, such as ellipsometric parameters, the thickness and refractive index of one or more films on the sample, or the critical dimensions (widths) of structures on the sample.

The arrangements of FIGS. 2(a) and 2(b) should be considered to be representative examples, as the use of fiber optics to reduce the effects of diffraction from any hard stops in the system can be applicable to a wide range of differing optical metrology tools, and is not limited to the specific combination(s) of components described with respect to FIGS. 2(a) and 2(b). In any of these tools, it can be desirable to position appropriate optical elements between the fiber and the pupil of a focusing objective to adjust the size of the illumination pattern on the pupil. Selective attenuation and mixing can be useful for systems where the illumination spot size is greater than, or smaller than, the measurement box size. In either case, the fiber can be used on either the collection or illumination sides to reduce the measurement spot size. In some systems, fibers can be used on both the collection and illumination sides in order to obtain an increase in performance.

It should be recognized that a number of variations of the above-identified embodiments will be obvious to one of ordinary skill in the art in view of the foregoing description. Accordingly, the invention is not to be limited by those specific embodiments and methods of the present invention shown and described herein. Rather, the scope of the invention is to be defined by the following claims and their equivalents.

What is claimed is:

1. A method of optically inspecting and evaluating a sample, comprising the steps of:
   illuminating a multimode optical fiber with a source of illumination;
   adjusting an angular spread of the illumination entering the optical fiber to be less than a numerical aperture of the optical fiber;
   configuring the optical fiber to control an amount of attenuation of illumination rays in the illumination, the amount of attenuation increasing with an increase in propagation angle of the illumination rays whereby the illumination exits the optical fiber as a probe beam having an angular spectrum with an intensity that is reduced at higher propagation angles relative to a central axis of the probe beam;
imaging the probe beam onto a measurement spot on the sample; and
analyzing a portion of the probe beam reflected from the measurement spot.

2. A method according to claim 1, further comprising:
selecting optical elements along the path of the probe beam such that none of the optical elements causes appreciable diffraction of the probe beam.

3. A method according to claim 1, further comprising:
placing an exit end of the optical fiber at a conjugate of the sample.

4. A method according to claim 1, wherein:
analyzing a portion of the reflected probe beam includes measuring at least one parameter selected from the group consisting of thickness, crystallinity, composition, and refractive index.

5. A method according to claim 1, further comprising:
imaging the portion of the probe beam reflected from the measurement spot onto a detector.

6. A method according to claim 1, further comprising:
selecting the multimode optical fiber in order to control the size of the measurement spot produced by the probe beam after exiting the optical fiber.

7. A method according to claim 1, further comprising:
selecting the multimode optical fiber in order to minimize the presence of secondary maxima about the measurement spot produced by the probe beam after exiting the optical fiber.

8. A method according to claim 1, wherein:
configuring the optical fiber includes controlling an amount of bending of the optical fiber, whereby the amount of attenuation and mixing of rays in the probe beam is controlled.

9. A method of optically inspecting and evaluating a sample, comprising the steps of:
illuminating a measurement spot on the sample with a probe beam;
collecting a portion of the probe beam reflected from the measurement spot and focusing the reflected probe beam onto an entrance end of a multimode optical fiber;
configuring the optical fiber to control an amount of attenuation of illumination rays in the reflected probe beam, the amount of attenuation increasing with an increase in propagation angle of the illumination rays whereby the probe beam exits the optical fiber having an angular spectrum with an intensity that is reduced at higher propagation angles relative to a central axis of the probe beam;
imaging the probe beam onto a detector; and
analyzing a portion of the probe beam reflected from the measurement spot.

10. A method according to claim 9, further comprising:
adjusting an angular spread of the reflected probe beam entering the multimode optical fiber.

11. A method according to claim 9, further comprising:
selecting optical elements along the path of the probe beam such that none of the optical elements causes appreciable diffraction of the probe beam.

12. A method according to claim 9, further comprising:
placing an entrance end of the optical fiber at a conjugate of the sample.

13. A method according to claim 9, wherein:
analyzing a portion of the probe beam includes measuring at least one parameter selected from the group consisting of thickness, crystallinity, composition, and refractive index.

14. A method according to claim 9, further comprising:
selecting the multimode optical fiber in order to control the size of the measurement spot measured by the detector.

15. A method according to claim 9, further comprising:
selecting the multimode optical fiber in order to minimize the presence of secondary maxima about the measurement spot measured by the detector.

16. A method according to claim 9, wherein:
configuring the optical fiber includes controlling an amount of bending of the optical fiber, whereby the amount of attenuation and mixing of rays in the probe beam is controlled.

17. A system for optically inspecting and evaluating a sample, comprising:
a light source for generating a probe beam;
an imaging element for imaging the probe beam onto a measurement spot on the sample;
a detection device for receiving a portion of the probe beam reflected from the measurement spot and generating an output signal in response thereto;
a multimode optical fiber positioned along a beam path of the probe beam; and
a focusing element positioned along the beam path and selected to adjust an angular spread of the probe beam to be less than a numerical aperture of the multimode optical fiber, wherein the optical fiber is configured to control an amount of attenuation of angled rays in the probe beam in order to control an angular distribution of rays of the probe beam exiting the optical fiber.

18. A system according to claim 17, wherein:
the optical fiber is positioned along the beam path between the light source and the sample, wherein an exit end of the optical fiber is positioned at a conjugate of the sample.

19. A system according to claim 17, wherein:
the optical fiber is positioned along the beam path between the sample and the detection device, wherein an entrance end of the optical fiber is positioned at a conjugate of the sample.

20. A system according to claim 17, wherein:
the multimode optical fiber adjusts the angular distribution of rays in the probe beam such that the brightness of a central region of a spot formed by the probe beam after exiting the fiber is more intense than the brightness of an edge region of the spot.

21. A system according to claim 20, wherein:
the brightness of the central region is at least 30% more intense than the brightness of the edge region.

22. A system according to claim 17, further comprising:
a collection focusing element for focusing the reflected probe beam onto the detection device.

23. A system according to claim 17, further comprising:
an optical collecting element for collecting the probe beam reflected from the sample.

24. A system according to claim 17, further comprising:
a processor for receiving the output signal from the detection device and determining at least one of a change in polarization state of the reflected probe beam, a change in magnitude of the reflected probe beam, and an optical scattering of the reflected probe beam.

25. A system according to claim 24, wherein:
the processor further determines at least one parameter selected from the group consisting of thickness, crystallinity, composition, and refractive index.

26. A system according to claim 17, further comprising:
an aperture placed along the beam path for limiting the geometric size of the measurement spot without causing an appreciable amount of diffraction.

27. A system according to claim 17, wherein:
an amount of bending of the optical fiber is adjustable to control the amount of attenuation and mixing of the probe beam.

28. A system according to claim 17, wherein:
an amount of bending of the optical fiber is adjustable to control the size of the measurement spot produced by the probe beam after exiting the optical fiber.

29. A system according to claim 17, wherein:
an amount of bending of the optical fiber is adjustable to minimize the presence of secondary maxima about the measurement spot produced by the probe beam after exiting the optical fiber.

30. A method of optically inspecting and evaluating a sample, comprising the steps of:
illuminating an entrance end of an optical fiber with a source of illumination, the illumination propagating along the optical fiber and exiting the optical fiber as a probe beam, the probe beam having an angular spectrum with an intensity that is reduced at higher propagation angles relative to a central axis of the probe beam;
collecting the probe beam and focusing the collected probe beam onto the sample using a set of optical elements, the probe beam substantially underfilling the set of optical elements such that there is no appreciable diffraction of the probe beam by the set of optical elements;
detecting light reflected from the sample to produce a measurement signal; and
analyzing the measurement signal in order to evaluate the sample.

31. A method according to claim 30, further comprising:
adjusting an angular spread of the illumination to be less than a numerical aperture of the optical fiber.

32. A method according to claim 30, further comprising:
selecting optical elements along the path of the probe beam such that none of the optical elements causes appreciable diffraction of the probe beam.

33. A method according to claim 30, further comprising:
placing an exit end of the optical fiber at a conjugate of the sample.

34. A method according to claim 30, wherein:
analyzing a portion of the probe beam includes measuring at least one parameter selected from the group consisting of thickness, crystallinity, composition, and refractive index.

35. A method according to claim 30, further comprising:
imaging the portion of the probe beam reflected from the measurement spot onto a detector.

36. A method according to claim 30, further comprising:
configuring the optical fiber in order to control the size of the measurement spot produced by the probe beam after exiting the optical fiber.

37. A method according to claim 36, wherein:
configuring the optical fiber includes controlling an amount of bending of the optical fiber, whereby the amount of attenuation and mixing of rays in the probe beam is controlled.

38. A method according to claim 30, further comprising:
selecting the optical fiber in order to minimize the presence of secondary maxima about the measurement spot produced by the probe beam after exiting the optical fiber.

39. A method of optically inspecting and evaluating a sample, comprising the steps of:
generating a probe beam to illuminate a measurement spot on a sample;
collecting light reflected from the measurement spot with at least one optical element, the at least one optical element producing diffracted light that propagates at an angle relative to a directional axis of the reflected light;
focusing the reflected light onto an entrance end of an optical fiber, the transmission of the reflected light in the optical fiber varying as a function of propagation angle such that light exiting the optical fiber has an angular spectrum with an intensity that is reduced at higher propagation angles relative to a central axis of the probe beam, the diffracted light contributing less to the light transmitted through the optical fiber than the light entering the optical fiber;
detecting the light transmitted through the optical fiber and generating an output signal in response thereto; and
analyzing the output signal in order to evaluate the sample.

40. A method according to claim 39, further comprising:
placing the entrance end of the optical fiber at a conjugate of the sample.

41. A method according to claim 39, further comprising:
adjusting an angular spread of the reflected light to be less than a numerical aperture of the optical fiber.

42. A method according to claim 39, wherein:
analyzing the output signal includes determining at least one parameter selected from the group consisting of thickness, crystallinity, composition, and refractive index.

43. A method according to claim 39, further comprising:
imaging the light exiting the optical fiber onto a detector.

44. A method according to claim 39, further comprising:
configuring the optical fiber in order to control the size of the measurement spot detected by a detector receiving the light exiting the optical fiber.

45. A method according to claim 39, wherein:
configuring the optical fiber includes controlling an amount of bending of the optical fiber, whereby the amount of attenuation and mixing of rays in the reflected light is controlled.

46. A method according to claim 39, further comprising:
selecting the optical fiber in order to minimize the presence of secondary maxima about the measurement spot detected by a detector receiving the light exiting the optical fiber.

* * * * *